United States Patent
Smith et al.

(10) Patent No.: US 11,840,671 B2
(45) Date of Patent: Dec. 12, 2023

(54) BIO-BASED OLEFIN OLIGOMERIZATION VIA CHABAZITE ZEOLITE CATALYST

(71) Applicant: Gevo, Inc., Englewood, CO (US)

(72) Inventors: Jonathan Smith, Highlands Ranch, CO (US); Madeline Sjodin, Denver, CO (US)

(73) Assignee: Gevo, Inc., Englewood, CO (US)

( * ) Notice: Subject to any disclaimer, the term of this patent is extended or adjusted under 35 U.S.C. 154(b) by 14 days.

(21) Appl. No.: 17/556,796

(22) Filed: Dec. 20, 2021

(65) Prior Publication Data

US 2022/0112434 A1    Apr. 14, 2022

Related U.S. Application Data

(63) Continuation of application No. PCT/US2020/039681, filed on Jun. 25, 2020.

(60) Provisional application No. 62/867,776, filed on Jun. 27, 2019.

(51) Int. Cl.
| | | |
|---|---|---|
| *C10G 50/00* | (2006.01) | |
| *B01J 29/85* | (2006.01) | |
| *B01J 38/02* | (2006.01) | |

(52) U.S. Cl.
CPC .............. *C10G 50/00* (2013.01); *B01J 29/85* (2013.01); *B01J 38/02* (2013.01); *C10G 2300/1011* (2013.01); *C10G 2300/4018* (2013.01); *C10G 2300/70* (2013.01); *C10G 2400/22* (2013.01)

(58) Field of Classification Search
CPC ............ C10G 50/00; C10G 2300/1011; C10G 2300/4018; C10G 2300/70; C10G 2400/22; C10G 3/00; C10G 3/49; C10G 2400/04; C10G 2400/08; B01J 29/85; B01J 38/02; C07C 2529/89; C07C 1/24; C07C 2/12; C10L 1/04

See application file for complete search history.

(56) References Cited

U.S. PATENT DOCUMENTS

| | | | |
|---|---|---|---|
| 4,613,719 A | 9/1986 | Kukes et al. | |
| 4,880,520 A | 11/1989 | Lok et al. | |
| 7,847,037 B2 * | 12/2010 | Simon | B01J 29/68 526/108 |
| 9,688,590 B2 | 6/2017 | Cross, Jr. et al. | |
| 2002/0111523 A1 * | 8/2002 | Mathys | C07C 2/10 585/524 |
| 2004/0015028 A1 * | 1/2004 | Brown | C10G 50/00 585/533 |
| 2005/0222475 A1 * | 10/2005 | Duplan | C07C 2/12 585/329 |
| 2006/0199987 A1 | 9/2006 | Kuechler et al. | |
| 2008/0139860 A1 | 6/2008 | Simon et al. | |
| 2013/0131411 A1 | 5/2013 | Blommel et al. | |
| 2014/0114101 A1 | 4/2014 | Greene et al. | |
| 2014/0249340 A1 * | 9/2014 | Tom | C10G 3/49 585/255 |
| 2016/0194572 A1 * | 7/2016 | Lilga | C07C 2/66 585/277 |
| 2017/0050896 A1 | 2/2017 | Yasukawa et al. | |
| 2017/0218283 A1 | 8/2017 | Lilga et al. | |

FOREIGN PATENT DOCUMENTS

EP    2 374 781 A1    10/2011

OTHER PUBLICATIONS

Fan, D. et al. (2013). "Ethylene Formation by Catalytic Dehydration of Ethanol with Industrial Considerations." Materials 6; No. 1: 101-115. https://doi.org/10.3390/ma6010101.

Ramesh, K. et al. (2009, e-published Nov. 5, 2008). "Structure and reactivity of phosphorus modified H-ZSM-5 Catalysts for ethanol dehydration." Catalysis Communications 10; 567-571.

* cited by examiner

*Primary Examiner* — Ali Z Fadhel
(74) *Attorney, Agent, or Firm* — Mintz Levin Cohn Ferris Glovsky and Popeo, P.C.

(57) ABSTRACT

This present disclosure relates to catalytic processes for oligomerizing bio-based olefinic mixtures to higher value renewable fuels via a doped Chabazite zeolite catalyst. A stream including a $C_2$-$C_8$ olefin and an oxygenate is fed to an oligomerization process utilizing a doped Chabazite zeolite catalyst resulting in high yields and selectivity of oligomers used to produce bio-based jet fuel and/or diesel fuels depending upon reaction temperatures and pressures. The process also produces iso-octane that is suitable for producing bio-based gasoline. The process tolerates relatively high levels of oxygenates in the olefinic feed and the catalyst is capable of air regeneration.

11 Claims, 1 Drawing Sheet

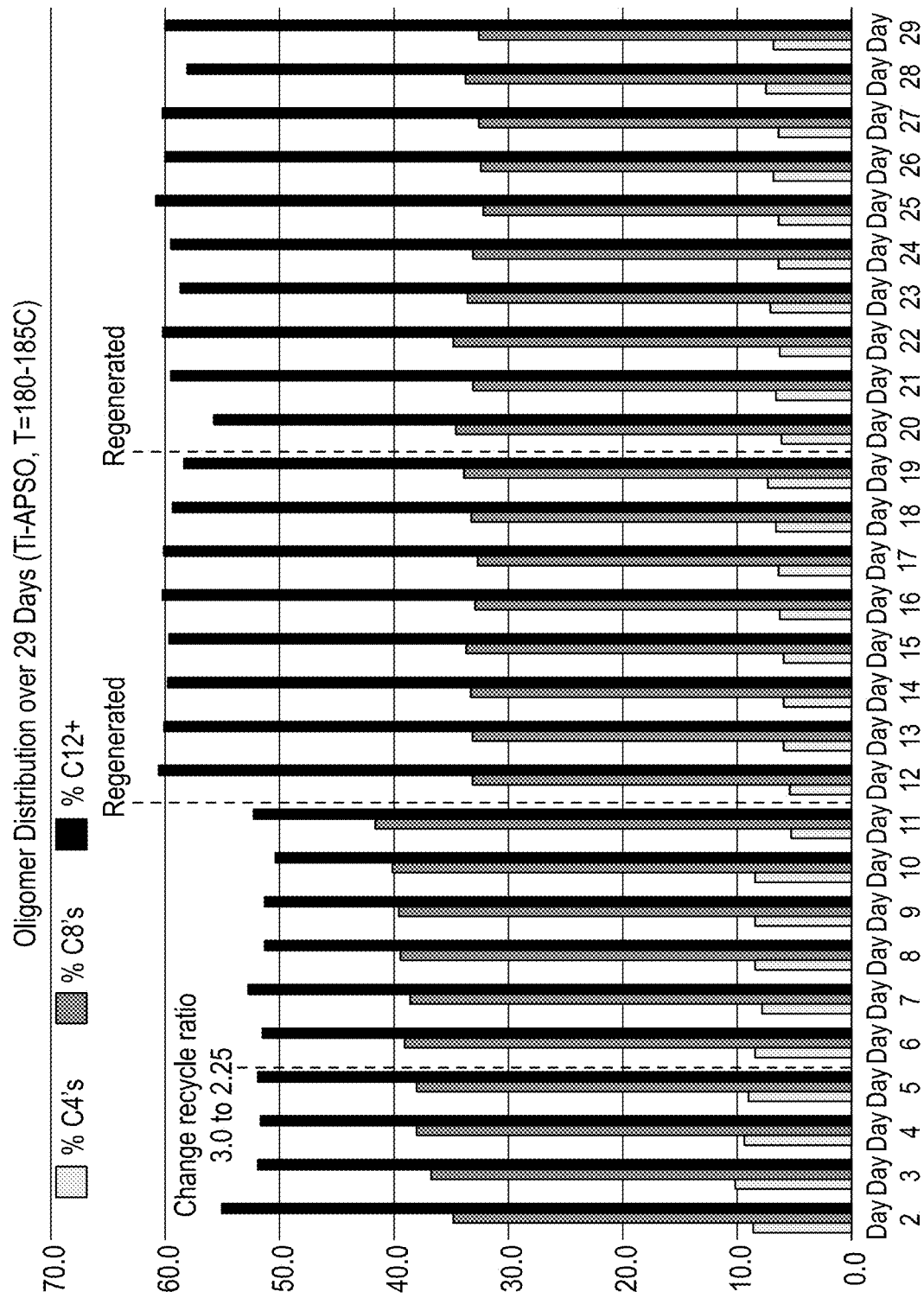

BIO-BASED OLEFIN OLIGOMERIZATION VIA CHABAZITE ZEOLITE CATALYST

CROSS-REFERENCES TO RELATED APPLICATIONS

This application is a bypass continuation of and claims priority to PCT Application No. PCT/US2020/039681, filed on Jun. 25, 2020, entitled "BIO-BASED OLEFIN OLIGOMERIZATION VIA CHABAZITE ZEOLITE CATALYST", which claims priority to U.S. Provisional Application No. 62/867,776 filed on Jun. 27, 2019, entitled "Olefin Oligomerization to Iso-Octane and Jet Fuel via Metal Doped Chabazite Zeolite", each of which is incorporated by reference in its entirety for all purposes.

TECHNICAL FIELD

The subject matter described herein relates to a process for converting lower linear and branched mono-olefins derived from $C_2$-$C_5$ bio-based alcohols to higher hydrocarbons, which are useful as precursors for iso-octane (i.e. gasoline), jet fuel, or diesel fuel production.

BACKGROUND OF THE INVENTION

Acceptance of biofuels in the diesel-fueled industries and aviation industry has lagged even farther behind that of the automotive industry. Methyl trans-esterified fatty acids from seed oils (such as soybean, corn, etc.) have several specific disadvantages compared to petroleum-derived diesel fuels, particularly the fact that insufficient amounts of seed oil are available. Even under the most optimistic scenarios, seed oils could account for no more than 5% of the overall diesel demand. Furthermore, for diesel and aviation engines, the cold flow properties of the long-chain fatty esters from seed oils are sufficiently poor so as to cause serious operational problems even when used at levels as low as 5% by weight. Under cold conditions, the precipitation and crystallization of fatty paraffin waxes can cause debilitating flow and filter plugging problems. For aviation engines, the high temperature instability of the esters and olefinic bonds in seed oils is also a potential problem. To use fatty acid esters for jet fuel, the esters must be hydrotreated to remove all oxygen and olefinic bonds. Additionally, jet fuels must contain aromatics in order to meet the stringent energy density and seal swelling demands of jet turbine engines. Accordingly, synthetic jet fuels including hydrotreated fatty acid esters from seed oils must be blended with aromatic compounds derived from fossil fuels to fully meet jet fuel specifications, and are therefore not entirely bio-based.

BRIEF SUMMARY OF THE INVENTION

Aspects of the current subject matter relate inter alia to processes for converting lower linear and branched mono-olefins derived from $C_2$-$C_5$ bio-based alcohols to higher hydrocarbons. Embodiments of the current subject matter provide improvements over conventional processes that are tailored for handling petroleum-derived feedstocks.

Consistent with some aspects of the current subject matter, a process for converting one or more $C_2$-$C_8$ linear or branched olefins derived from one or more $C_2$-$C_5$ alcohols to one or more $C_8$-$C_{24}$ hydrocarbons is disclosed. The process includes contacting a feed stream comprising the one or more $C_2$-$C_8$ linear or branched olefins, and an oxygenate, with a doped Chabazite zeolite catalyst at a temperature of 100 to 300° C., a pressure of 100 to 600 psig and a WHSV of at least 1.5, and forming the one or more $C_8$-$C_{24}$ hydrocarbons. The yield of the one or more $C_8$-$C_{24}$ hydrocarbons is at least 90%.

In optional variations, one or more of the following features may be included in any feasible combination. For example, the feed stream may include at least 100 ppm of oxygenates. The oxygenates may include water, $C_2$-$C_5$ alcohol, or a combination thereof. The one or more $C_2$-$C_8$ linear or branched olefins in the feed stream can be one or more $C_2$-$C_5$ olefins. In embodiments, the one or more $C_8$-$C_{24}$ hydrocarbons are one or more $C_{8-16}$ hydrocarbons. In embodiments, the yield of the one or more $C_8$-$C_{24}$ hydrocarbons are at least about 95%. In embodiments, the yield of the $C_8$ hydrocarbon is at least about 35%. In embodiments, the yield of the $C_{12}$ hydrocarbon is at least about 40%. In embodiments, a selectivity of $C_8$ to $C_{12}$ and larger oligomers is at least 0.30:1, including all subranges therein.

Consistent with some aspects of the current subject matter, the Chabazite zeolite catalyst is a doped Chabazite zeolite catalyst. The doped Chabazite zeolite catalyst can be regenerated in air every 5 to 20 days, including all subranges therein. The doped Chabazite zeolite catalyst can be regenerated at a temperature of 400 to 600° C., including all subranges therein. The doped Chabazite zeolite catalyst can be regenerated in 30 minutes to 3 hours, including all subranges therein.

Consistent with some aspects of the current subject matter, a process for converting one or more $C_2$-$C_8$ linear or branched olefins to one or more $C_8$-$C_{24}$ hydrocarbons is disclosed. The process operates at a reaction temperature of 100 to 260° C., and a reaction pressure of 200 to 500 psig, including all subranges therein. The WHSV for the process can be at least 1.5.

Consistent with some aspects of the current subject matter, the present process provides for converting one or more $C_2$-$C_8$ linear or branched olefins derived from one or more $C_2$-$C_5$ alcohols to one or more $C_8$-$C_{24}$ hydrocarbons. The process includes contacting a feed stream comprising the one or more $C_2$-$C_8$ linear or branched olefins, and an oxygenate, with a doped Chabazite zeolite catalyst at a temperature of 100 to 300° C., at a pressure of 100 to 600 psig and at a WHSV of at least 1.5, thus forming the one or more $C_8$-$C_{24}$ hydrocarbons with a yield of at least 90%. In embodiments, the feed stream further consists of a non-fossil fuel and non-petroleum derived fuel, or a combination thereof. In embodiments, the feed stream includes a recycled feed stream containing a portion of a product stream comprising one or more $C_8$-$C_{24}$ hydrocarbons.

Consistent with some aspects of the current subject matter, a process for converting one or more $C_2$-$C_8$ linear or branched olefins derived from one or more $C_2$-$C_5$ alcohols to one or more $C_8$-$C_{24}$ hydrocarbons is disclosed. The process includes contacting a feed stream comprising the one or more $C_2$-$C_8$ linear or branched olefins and at least 1000 ppm of an oxygenate, with a doped Chabazite zeolite catalyst at a temperature of 150 to 200° C., a pressure of 200 to 300 psig and a WHSV of between 2 and 3.2, and forming the one or more $C_8$-$C_{24}$ hydrocarbons, with a yield of the one or more $C_8$-$C_{24}$ hydrocarbons being at least 90% and a selectivity of $C_8$ to $C_{12}$ and larger oligomers is at least 0.35:1. The oxygenate includes water and at least one alcohol, and the doped Chabazite zeolite catalyst comprises TiAPSO-34.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWING

The accompanying drawing, which is incorporated into and constitute a part of this specification, show certain aspects of the subject matter disclosed herein and, together with the description, help explain some of the principles associated with the disclosed implementations. In the drawing:

FIG. 1 is a graph of oligomer distribution results for extended time on stream with oxygenates and multiple catalyst regenerations, in which $C_4$ is the first bar, $C_8$ is the $2^{nd}$ bar, and $C_{12+}$ is the $3^{rd}$ bar for each day, left to right in the graph.

DETAILED DESCRIPTION

In the following description, certain specific details are set forth in order to provide a thorough understanding of various embodiments. However, one skilled in the art will understand that the disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The word "about" when immediately preceding a numerical value means a range of plus or minus 10% of that value, e.g., "about 50" means 45 to 55, "about 25,000" means 22,500 to 27,500, etc. Furthermore, the phrases "less than about" a value or "greater than about" a value should be understood in view of the definition of the term "about" provided herein.

"Oxygenate" refers to compounds which include oxygen in their chemical structure. Examples of oxygenates include, but are not limited to water, alcohols, esters, and ethers.

"WHSV" refers to weight hourly space velocity and is defined as the weight of the feed flowing per unit weight of the catalyst per hour.

All yields and conversions described herein are on a mass basis unless specified otherwise.

Powdered, granular, and/or extruded doped Chabazite zeolite catalysts are suitable for the reactions even though no specific size and morphology are mandatory. Catalyst with a size greater than 0.1 mm is more suitable, and the size of 0.2-1.0 mm is most suitable for the operation ability and low pressure drop. Catalysts according to the present disclosure can have CZC structure type with a composition comprising $SiO_2$ and $Al_2O_3$. The composition of the catalyst can further comprise titanium and phosphorus within the framework. The doped Chabazite zeolite catalysts have high surface area microporosity, such as values greater than 400 $m^2/g$. The pore structure of the catalyst is 3-dimensional with an opening of about 4 angstroms. The catalyst is highly water-stable and able to withstand hydrothermal conditions.

Disclosed herein is a novel oligomerization processes utilizing a doped Chabazite zeolite catalyst in a reaction resulting in mixed olefin conversions to higher hydrocarbons in yields of at least 90%. Accordingly, an objective is to provide a process for producing $C_8$-$C_{24}$ hydrocarbon oligomers using a doped Chabazite zeolite catalyst with a superior catalytic regeneration rate and high yield of $C_8$-$C_{24}$ hydrocarbons. Embodiments, according to the present process, convert one or more $C_2$-$C_8$ linear or branched olefins derived from one or more $C_2$-$C_5$ alcohols to one or more $C_8$-$C_{24}$ hydrocarbons in a variety of ways as described herein.

Fermentation processes are suitable for producing bio-based $C_2$-$C_5$ alcohols and mixtures thereof. Dehydration of $C_2$-$C_5$ alcohols, and in some cases their subsequent isomerization, is known, but few reports target catalysts aimed at dehydrating mixtures of bio-based $C_2$-$C_5$ alcohols directly followed by oligomerization to jet and/or diesel fuels in a fully integrated mode. The oligomerization of gaseous mono-olefins to form gasoline, jet, and diesel-type hydrocarbons is also known, particularly for feed streams obtained from petroleum derived sources. However, there is an ever present need to develop new oligomerization processes employing more stable, effective, and/or less expensive catalyst compositions that may be utilized with bio-based olefinic streams containing high levels of oxygenates thereby eliminating the need for expensive treatment and/or purification processes prior to oligomerization. Aspects of the current subject provide for the production of improved renewable jet fuel blend stocks and jet fuel blends with costs and performance properties comparable to, or superior to, existing petroleum-derived jet fuels, and which meet or exceed the requirements of ASTM D7566-10a for aviation turbine fuel containing synthetic hydrocarbons.

In embodiments, $C_2$-$C_8$ olefin oligomerization processes via a doped Chabazite zeolite catalyst result in high yield and selectivity to produce bio-based iso-octane and jet fuel at relatively low temperatures and pressures, while tolerating high levels of oxygenates in the olefinic feed. Other catalysts for $C_2$-$C_8$ linear olefin oligomerization, such as natural zeolites, modified zeolites, SPA's, and Nafion resins, deactivate rapidly requiring re-activation, are relatively expensive to purchase, have poor tolerance for the presence of oxygenates, and result in higher levels of oligomer cracking/isomerization as evidenced by higher levels of $C_5$-$C_7$ species and lesser amounts of isolated yields to iso-octane and jet fuel fractions.

The presence of relatively high levels of alcohol, water, and other oxygenates in a feed stream, which would be expected to result in commercially unacceptable low product yields, has been surprisingly found to not result in catalyst deactivation when a doped Chabazite zeolite catalyst is used under certain reaction conditions. Yields of $C_{12}+$ oligomers (i.e. fractions suitable for the production of jet fuel) of at least 50% can be maintained, while simultaneously producing 35-40% $C_8$ oligomers (i.e. iso-octane for gasoline) without pre-purification of a crude $C_2$-$C_5$ alcohols feed (i.e. isobutylene rich feed stream) to an oligomerization unit. Moreover, near complete single-pass isobutylene conversion can results from embodiments of the present process.

Oligomerization of crude renewable $C_2$-$C_5$ alcohols (i.e. butylenes) containing relatively high levels of water, alcohols, and other oxygenates to jet fuel proceeds smoothly over the doped Chabazite zeolite catalyst. The capital expenditure and variable cost of a commercial jet fuel production unit is significantly reduced by not requiring purification of the "crude" olefinic stream obtained from the dehydration of renewable isobutanol, prior to oligomerization. Typically, so-called "modifiers," including of alcohols, water, and other oxygenates, are purposely added to the feed steam of the oligomerization unit to reduce catalytic activity therein, enabling selective formation of high levels of $C_8$ hydrocarbons in proportion to $C_{12}$ and larger oligomers. As such, the addition of modifiers, typically results in unacceptably low yields to jet fuel (i.e. $C_{12}$ and higher hydrocarbons) with a corresponding high yield to $C_8$ hydrocarbons including iso-octane. In embodiments, $C_2$-$C_8$ olefin oligomerization processes via doped Chabazite zeolite catalyst do not require the addition of modifiers.

Another advantage consistent with aspects of the current subject matter, is the ability to regenerate the doped Chabazite zeolite catalyst via air heated 500° C. for 1-2 hours in order to return the catalyst to initial activity as needed. One skilled in the art will immediately recognize the commercial applications and advantages of a process including a catalyst which maintains activity in the presence of oxygenates and that can be regenerated when catalyst deactivation is observed. Additionally, higher reaction temperatures can be used with the present process to result in the selective formation of more diesel precursor oligomers than with other processes using different catalysts.

Higher-chained hydrocarbons, such as $C_8$-$C_{24}$ hydrocarbons can be utilized for producing jet fuel or diesel fuel. The present process can produce higher-chained hydrocarbons, such as, but not limited to $C_8$-$C_{24}$ hydrocarbons in surprisingly high yield and selectivity to produce renewable jet fuel and or renewable diesel fuel. The present process further comprises separating and/or blending the one or more $C_8$-$C_{24}$ hydrocarbons to produce a renewable jet fuel or a renewable diesel fuel.

The present process is suitable for use with a variety of feed streams, including those with oxygenates, to produce the higher-chained hydrocarbons of the present invention. For example, the feed stream can further comprise crude products or by-products such as fusel oils, residual alcohols, water, and a recycled feed stream of a portion of the one or more $C_8$-$C_{24}$ hydrocarbons.

In embodiments, the one or more $C_2$-$C_5$ alcohols are bio-based and produced by fermentation processes. Fermentation processes include conversion of sugars into alcohols. Aspects of the present subject matter contain feed streams with non-fossil-fuel and non-petroleum-derived sources. While the present process may be suitable for petroleum-derived olefinic feed streams, the present process is particularly suitable for bio-based olefinic feed streams that contain oxygenates.

The oxygenates described herein can comprise any oxygenates such as organic and inorganic oxygenates. For example, organic oxygenates include, but are not limited to alcohols, esters, and ethers. Inorganic oxygenates include, but are not limited to, water. The oxygenates can comprise both water and lower carbon alcohols such as $C_2$-$C_5$ alcohols.

The feed stream can include at least 100 ppm of the oxygenate. In embodiments, the feed stream comprises at least 500 ppm of the oxygenate. In embodiments, the feed stream comprises at least 1000 ppm of the oxygenate. In embodiments, the feed stream comprises at least 1500 ppm of the oxygenate. In embodiments, the feed stream comprises at least 2000 ppm of the oxygenate. In embodiments, the feed stream comprises at least 2500 ppm of the oxygenate. In embodiments, the feed stream comprises at least 3000 ppm of the oxygenate. In embodiments, the feed stream comprises at least 4000 ppm of the oxygenate. In embodiments, the feed stream comprises at least 5000 ppm of the oxygenate. In embodiments, the feed stream comprises at least 7000 ppm of the oxygenate. In embodiments, the feed stream comprises at least 10000 ppm of the oxygenate.

The feed stream can include between 100 ppm to 10000 ppm of the oxygenate. In embodiments, the feed stream comprises between 1000 ppm to 7000 ppm of the oxygenate. In embodiments, the feed stream comprises between 2000 ppm to 7000 ppm of the oxygenate.

The feed stream can include at least 100 ppm of water. In embodiments, the feed stream comprises at least 200 ppm of water. In embodiments, the feed stream comprises at least 300 ppm of water. In embodiments, the feed stream comprises at least 500 ppm of water. In embodiments, the feed stream comprises between 100 to 300 ppm of water. In embodiments, the feed stream comprises between 100 to 200 ppm of water.

The feed stream can include at least 1000 ppm of the one or more $C_2$-$C_5$ alcohols. In embodiments, the feed stream comprises at least 1500 ppm of the one or more $C_2$-$C_5$ alcohols. In embodiments, the feed stream comprises at least 3000 ppm of the one or more $C_2$-$C_5$ alcohols. In embodiments, the feed stream comprises at least 5000 ppm of the one or more $C_2$-$C_5$ alcohols. In embodiments, the feed stream comprises at least 6000 ppm of the one or more $C_2$-$C_5$ alcohols. In embodiments, the feed stream comprises at least 7000 ppm of the one or more $C_2$-$C_5$ alcohols. In embodiments, the feed stream comprises between 1000 ppm to 7000 ppm of the one or more $C_2$-$C_5$ alcohols. In embodiments, the feed stream comprises between 1500 ppm to 6500 ppm of the one or more $C_2$-$C_5$ alcohols.

In embodiments, the one or more $C_2$-$C_5$ alcohols are $C_4$ alcohols. In embodiments, the one or more $C_2$-$C_5$ alcohols are selected from the group consisting of ethanol, n-propanol, isopropanol, n-butanol, sec-butanol, isobutanol, tert-butanol, n-pentanol, 2-pentanol, 3-pentanol, 2-methylbutan-1-ol, 3-methylbutan-1-ol, 2-methylbutan-2-ol, 2-methylbutan-3-ol, 2,2-dimethylpropanol, or a combination thereof. In embodiments, the one or more $C_2$-$C_5$ alcohols are selected from the group consisting of butanol, sec-butanol, isobutanol, tert-butanol, or a combination thereof. In embodiments, the one or more $C_2$-$C_5$ alcohols are selected from the group consisting of isobutanol, tert-butanol, or a combination thereof.

The feed stream can include the oxygenate selected from the group consisting of ethanol, n-propanol, isopropanol, n-butanol, sec-butanol, isobutanol, tert-butanol, n-pentanol, 2-pentanol, 3-pentanol, 2-methylbutan-1-ol, 3-methylbutan-1-ol, 2-methylbutan-2-ol, 2-methylbutan-3-ol, 2,2-dimethylpropanol, water, or a combination thereof. In embodiments, the feed stream comprises the oxygenate selected from the group consisting of butanol, sec-butanol, isobutanol, tert-butanol, water, or a combination thereof. In embodiments, the feed stream comprises the oxygenate selected from the group consisting of isobutanol, tert-butanol, water, or a combination thereof.

The olefins described herein are any olefins composed of $C_2$ or higher carbon, preferentially to be branched and/or linear $C_2$-$C_8$ mixtures of unsaturated hydrocarbons. The olefins can be mixtures of ethylene ($C_2H_4$), propylene ($C_3H_6$), butylenes ($C_4H_8$), pentenes ($C_5H_{10}$), and hexenes ($C_6H_{12}$) as the most suitable olefins. The olefins described herein can be in a liquid or gas phase at standard conditions.

In embodiments, the one or more $C_2$-$C_8$ linear or branched olefins are one or more $C_2$-$C_5$ olefins. In embodiments, the one or more $C_2$-$C_8$ linear or branched olefins are one or more $C_4$ olefins. In embodiments, the one or more $C_2$-$C_8$ linear or branched olefins is but-1-ene, (2Z)-but-2-ene, (2E)-but-2-ene, 2-methylprop-1-ene, or a combination thereof. In embodiments, the one or more $C_2$-$C_8$ linear or branched olefins is (2Z)-but-2-ene, (2E)-but-2-ene, 2-methylprop-1-ene, or a combination thereof.

The present process provides production of higher-chained hydrocarbons such as $C_8$-$C_{24}$ hydrocarbons in unexpectedly high yield. The present process can also provide high yields of $C_8$ hydrocarbons without the need for pre-purification of a crude feed stream.

In embodiments, the one or more $C_8$-$C_{24}$ hydrocarbons are one or more $C_{8-16}$ hydrocarbons. In embodiments, the one or more $C_8$-$C_{24}$ hydrocarbons are one or more $C_{8-12}$ hydrocarbons. In embodiments, the one or more $C_8$-$C_{24}$ hydrocarbons are $C_8$ hydrocarbons, $C_{12}$ hydrocarbons, $C_{16}$ hydrocarbons, or a combination thereof. In embodiments, the one or more $C_8$-$C_{24}$ hydrocarbons are $C_8$ hydrocarbons, $C_{12}$ hydrocarbons, or a combination thereof.

It has been surprisingly found that even in the presence of oxygenates, the yields of higher-chained hydrocarbons did not significantly change when using the doped Chabazite zeolite catalyst. Yields of $C_8$-$C_{24}$ hydrocarbons were found to be about 90% or more. Yields of $C_{12}$ and longer chained hydrocarbons ($C_{12}$+) had a yield about at least 50%, while simultaneously producing about 35-40% of $C_8$ hydrocarbons.

In embodiments, the yield of the one or more $C_8$-$C_{24}$ hydrocarbons are at least about 90%. In embodiments, the yield of the one or more $C_8$-$C_{24}$ hydrocarbons are at least about 95%. In embodiments, the yield of the one or more $C_8$-$C_{24}$ hydrocarbons are at least about 97%.

In embodiments, the yield of the one or more $C_8$ hydrocarbons is at least about 30%. In embodiments, the yield of the one or more $C_8$ hydrocarbons is at least about 35%. In embodiments, the yield of the one or more $C_8$ hydrocarbons is at least about 40%. In embodiments, the yield of the one or more $C_8$ hydrocarbons is between 30% to 40%. In embodiments, the yield of the one or more $C_8$ hydrocarbons is between 35% to 40%.

In embodiments, the yield of the one or more $C_{12}$ hydrocarbons is at least about 40%. In embodiments, the yield of the one or more $C_{12}$ hydrocarbons is at least about 45%. In embodiments, the yield of the one or more $C_{12}$ hydrocarbons is at least about 50%. In embodiments, the yield of the one or more $C_{12}$ hydrocarbons is at least about 60%. In embodiments, the yield of the one or more $C_{12}$ hydrocarbons is between 40% to 65%. In embodiments, the yield of the one or more $C_{12}$ hydrocarbons is between 45% to 60%. In embodiments, the yield of the one or more $C_{12}$ hydrocarbons is between 45% to 50%.

The present process provides production of higher-chained hydrocarbons such as $C_8$-$C_{24}$ hydrocarbons with unexpectedly high selectivity, regardless of whether oxygenates are present or absent. High yields of $C_8$ hydrocarbon oligomers to $C_{12}$ hydrocarbon oligomers can be obtained by the process as described in the present invention. For example the ratio of $C_8$ to $C_{12}$ hydrocarbons can be between 0.35:1 to 0.8:1, 0.5:1 to 0.8:1, 0.6:1 to 0.8:1, or 0.7:1 to 0.8:1. In embodiments, the ratio of $C_8$ to $C_{12}$ hydrocarbons can be between 0.6:1 to 0.8:1. In embodiments, the ratio of $C_8$ to $C_{12}$ hydrocarbons can be between 0.7:1 to 0.8:1.

In embodiments, the present process has a selectivity of $C_8$ to $C_{12}$ and larger oligomers of at least 0.30:1. In embodiments, the present process has a selectivity of $C_8$ to $C_{12}$ and larger oligomers of at least 0.35:1. In embodiments, the present process has a selectivity of $C_8$ to $C_{12}$ and larger oligomers of at least 0.40:1. In embodiments, the present process has a selectivity of $C_8$ to $C_{12}$ and larger oligomers of at least 0.45:1. In embodiments, the present process has a selectivity of $C_8$ to $C_{12}$ and larger oligomers of at least 0.5:1. In embodiments, the present process has a selectivity of $C_8$ to $C_{12}$ and larger oligomers of at least 0.6:1. In embodiments, the present process has a selectivity of $C_8$ to $C_{12}$ and larger oligomers of at least 0.7:1. In embodiments, the present process has a selectivity of $C_8$ to $C_{12}$ and larger oligomers of between 0.35:1 to 0.7:1. In embodiments, the present process has a selectivity of $C_8$ to $C_{12}$ and larger oligomers of between 0.5:1 to 0.7:1. In embodiments, the present process has a selectivity of $C_8$ to $C_{12}$ and larger oligomers of between 0.6:1 to 0.7:1.

Oligomerization of $C_2$-$C_8$ olefins containing high levels of water, alcohols, and other oxygenates to $C_8$-$C_{24}$ hydrocarbons proceeds smoothly over a doped Chabazite zeolite catalyst. Moreover, oligomerization of 'crude' olefinic streams in the presence of the doped Chabazite zeolite catalyst, without purification to remove oxygenates and/or water, results in formation of $C_8$-$C_{24}$ hydrocarbons in unexpectedly high yields.

Efforts aimed at producing $C_8$-$C_{24}$ hydrocarbons in high yields from $C_2$-$C_8$ olefins identified a selective oligomerization process resulting in exemplary mass yields to $C_8$-$C_{24}$ hydrocarbons exceeding at least 90%. Surprisingly, the oligomerization process can be operated at relatively low temperatures and pressures with doped Chabazite zeolite catalysts. Specifically, the oligomerization of $C_2$-$C_8$ olefins on the doped Chabazite zeolite catalyst proceeds smoothly at reaction pressures of 250-600 prig, reaction temperatures of 170-350° C., and a WHSV of 2.0-3.2 resulting in a single pass olefin conversion of at least 90%. In addition, the doped Chabazite zeolite catalyst can be easily regenerated via air to regain activity.

In embodiments, the Chabazite zeolite catalyst is a doped Chabazite zeolite catalyst. In embodiments, the doped Chabazite zeolite catalyst comprises titanium and phosphorus. In embodiments, the doped Chabazite zeolite catalyst is TiAPSO-34, which is commercially available from Clariant AG.

The doped Chabazite zeolite catalyst can be regenerated in air. In embodiments, the doped Chabazite zeolite catalyst is regenerated in air every 5 to 20 days.

The doped Chabazite zeolite catalyst can be regenerated at variety of temperatures and times as described herein. In embodiments, the doped Chabazite zeolite catalyst is regenerated at a temperature of 400 to 700° C. In embodiments, the doped Chabazite zeolite catalyst is regenerated at a temperature of 400 to 600° C. In embodiments, the doped Chabazite zeolite catalyst is regenerated at a temperature of about 500° C. In embodiments, the doped Chabazite zeolite catalyst is regenerated in 30 minutes to 3 hours. In embodiments, the doped Chabazite zeolite catalyst is regenerated in 1 to 2 hours. In embodiments, the doped Chabazite zeolite catalyst is regenerated in about 2 hours. In embodiments, the doped Chabazite zeolite catalyst is regenerated in about 1 to 2 hours at a temperature of about 500° C.

The reaction temperature for converting $C_2$-$C_8$ linear or branched olefins to $C_8$-$C_{24}$ hydrocarbons can be any reaction temperature known by one of skill in the art. Relatively low temperatures has unexpectedly resulted in high yield and selectivity of higher-chained hydrocarbons such as $C_8$-$C_{24}$ hydrocarbons.

In embodiments, the reaction temperature for converting $C_2$-$C_8$ linear or branched olefins to $C_8$-$C_{24}$ hydrocarbons is 100 to 260° C. In embodiments, the reaction temperature for converting $C_2$-$C_8$ linear or branched olefins to $C_8$-$C_{24}$ hydrocarbons is 150 to 200° C. In embodiments, the reaction temperature for converting $C_2$-$C_8$ linear or branched olefins to $C_8$-$C_{24}$ hydrocarbons is 180 to 185° C. In embodiments, the reaction temperature for converting $C_2$-$C_8$ linear or branched olefins to $C_8$-$C_{24}$ hydrocarbons is about 180° C.

The reaction pressure for converting $C_2$-$C_8$ linear or branched olefins to $C_8$-$C_{24}$ hydrocarbons can be any reaction temperature known by one of skill in the art. Relatively low reaction pressure has surprisingly resulted in high yields and selectivity of higher-chained hydrocarbons such as $C_8$-$C_{24}$ hydrocarbons.

In embodiments, the pressure for converting $C_2$-$C_8$ linear or branched olefins to $C_8$-$C_{24}$ hydrocarbons is 200 to 500 psig. In embodiments, the reaction pressure for converting $C_2$-$C_8$ linear or branched olefins to $C_8$-$C_{24}$ hydrocarbons is 200 to 400 psig. In embodiments, the reaction pressure for converting $C_2$-$C_8$ linear or branched olefins to $C_8$-$C_{24}$ hydrocarbons is 200 to 300 psig. In embodiments, the reaction pressure for converting $C_2$-$C_8$ linear or branched olefins to $C_8$-$C_{24}$ hydrocarbons is about 250 psig.

In embodiments, the reaction temperature and reaction pressure for converting $C_2$-$C_8$ linear or branched olefins to $C_8$-$C_{24}$ hydrocarbons can be in any combination as described above. In embodiments, the reaction temperature for converting $C_2$-$C_8$ linear or branched olefins to $C_8$-$C_{24}$ hydrocarbons is about 180° C. and the reaction pressure is about 250 psig. In embodiments, the reaction temperature for converting $C_2$-$C_8$ linear or branched olefins to $C_8$-$C_{24}$ hydrocarbons is 150 to 200° C. and the reaction pressure is 200 to 300 psig.

In embodiments, the reaction temperature and reaction pressure of the reaction, and the catalyst regeneration times and temperatures can be in any combination as described above. In embodiments, the reaction temperature for converting one or more $C_2$-$C_8$ linear or branched olefins to one or more $C_8$-$C_{24}$ hydrocarbons is 150 to 200° C., the reaction pressure is 200 to 300 psig, the catalyst is regenerated every 5 to 20 days, and wherein the catalyst is regenerated at a temperature of 400 to 600° C. in 1 to 2 hours. In embodiments, the reaction temperature for converting the one or more $C_2$-$C_8$ linear or branched olefins to one or more $C_8$-$C_{24}$ hydrocarbons is about 180° C., the pressure is about 250 psig, the catalyst is regenerated every 5 to 20 days, and wherein the catalyst is regenerated at a temperature of about 500° C. in about 2 hours.

Tuning the weight hourly space velocity (WHSV) can adjust the ratio of $C_{8-24}$ hydrocarbons. If the reactor is operating at too high a WHSV, with too low a recycle ratio, it can result in over oligomerization as observed by unacceptably high levels of $C_{16}$ and larger oligomers relative to the $C_{12}$ oligomers in a product stream. These higher levels of $C_{16}$ and larger oligomers result in a higher viscosity product that does not meet typical jet fuel specification viscosity requirements, and necessitates an additional separation step (e.g., vacuum distillation) to remove a portion of the $C_{16}$ oligomers, thus resulting in lower overall yields to jet fuel. Thus, tuning the WHSV is important for maintain the $C_8/C_{12}/C_{16}/C_{20}$ ratios.

In embodiments, the WHSV is at least 1.5. In embodiments, the WHSV is at least 2. In embodiments, the WHSV is at least 2.5. In embodiments, the WHSV is at least 3. In embodiments, the WHSV is at least 3.5. In embodiments, the WHSV is between 2 and 3.5. In embodiments, the WHSV is between 2.6 and 3.2.

In embodiments, the present process is for converting one or more $C_2$-$C_8$ linear or branched olefins derived from one or more $C_2$-$C_5$ alcohols to one or more $C_8$-$C_{24}$ hydrocarbons, the process comprising: contacting a feed stream comprising the one or more $C_2$-$C_8$ linear or branched olefins and at least 1000 ppm of an oxygenate, with a doped Chabazite zeolite catalyst at a reaction temperature of 150 to 200° C., a reaction pressure of 200 to 300 psig and a WHSV of between 2 and 3.2; and forming the one or more $C_8$-$C_{24}$ hydrocarbons, wherein a yield of the one or more $C_8$-$C_{24}$ hydrocarbons is at least 90% and a selectivity of $C_8$ to $C_{12}$ and larger oligomers is at least 0.35:1, wherein the oxygenate comprises water and at least one alcohol and the doped Chabazite zeolite catalyst comprises TiAPSO-34.

Examples

Reactor Setup

The oligomerization reaction of olefins was carried out at between 110 to 250° C. by using a fixed bed reactor containing 2.9 g of specified catalyst and flowing the liquefied olefins downward at a constant pressure of between 200 to 500 psig. The flow rates of hydrocarbons were controlled by Teledyne Model 500D syringe pumps coupled with D-Series pump controllers, and the olefin flow rate was adjusted to obtain the targeted olefin WHSV (weight hourly space velocity). The reaction temperature was maintained constant via a Lindberg Blue M furnace as manufactured by Thermo-Scientific. Olefin conversion was calculated by analysis of the liquid phase reactor effluent by gas chromatography for olefin content and comparing mass accountability fed versus liquid mass collected. Catalyst screening required that mass accountabilities exceeded 90% for continued development and evaluation. Tables 1 and 2 below provide oligomerization results utilizing a 90% isobutylene stream containing ~10% linear butenes with and without oxygenates present at conditions provided. Table 3 provides oligomerization results for extended time on stream (TOS) after 30 days and three regeneration cycles at 500° C. for 2 hours under air.

In embodiments, olefin oligomerization reaction temperature of branched and/or linear $C_2$-$C_5$ olefins is from 100° C. to 260° C., with reaction pressures ranging from 200-400 psig. In a typical reaction, after gaining reaction pressure and temperature, the fresh olefinic feed is metered at a specified flow rate and mixed with a specific flow of recycle in a mass ratio of 2-parts recycle to 1-part fresh olefinic feed. Based on the total mass in versus the total mass collected over a specific time period mass accountability is calculated based on gas chromatographic analysis of the collected product. Relatively low levels of butenes in the collected product coupled with high mass accountabilities indicates high butylene conversion and yield to $C_8+$ oligomers as indicated in the results presented in Tables 1-3.

Example 1: No Oxygenates and No Recycled Feed

Catalyst Clariant TiAPSO-34, Total WHSV=2; Reactor Top 180-185° C.; P (psig)=250; 2.9 g Clariant TiAPSO-34 (granular pellets)+glass beads; Mass Accountability=97.4%; Feed: 88% iC4; 6% cis-2-butene; 6% trans-2-butene.

As shown in Table 1 below, when the feed stream has been purified and refined to remove oxygenates and no recycled feed is used, the percentage of $C_8$ oligomers is about 40% and the percentage of $C_{12}$ oligomers is about 50%. Further, the percentage of $C_8$ and higher carbon chained ($C_8+$) oligomers is about 95%. The selectivity of $C_8$ to $C_{12}$ and larger oligomers is 0.69:1 and the yield of $C_8$-$C_{24}$ hydrocarbons is greater than 95%. The yield of $C_8$ hydrocarbons is greater than 39% and the yield of $C_{12}$ hydrocarbons is greater than 49%.

TABLE 1

Reaction oligomer product distribution:

| % C4 | % C5-C7 | % C8 | % C9-C11 | % C12 | % C13-C15 | % C16 | % C20 | % C24 |
|---|---|---|---|---|---|---|---|---|
| 3.96 | 0.42 | 39.04 | 0.35 | 49.26 | 0.12 | 6.43 | 0.41 | 0.01 |

Example 2: With Oxygenates and Recycled Feed

Catalyst Clariant TiAPSO-34, Total WHSV=3.2, Mass ratio recycle: fresh feed 3:1; Reactor Top 180-185° C., P (psig)=250; 2.9 g Clariant TiAPSO-34 (granular pellets)+glass beads; Mass Accountability=97.0%; Oxygenates in Recycle: 200 ppm water, 6070 ppm (isobutanol and tert-butyl alcohol); Feed: 88% iC4; 6% cis-2-butene; 6% trans-2-butene.

Table 2 illustrates the distribution of carbon oligomers with the feed stream comprises oxygenates such as alcohols and water, and about 25% of the feed stream comprises a recycled feed. The recycle feed comprises about 37% $C_8$ oligomers and about 47% $C_{12}$ oligomers. The percentage of $C_8+$ oligomers in the recycle feed is greater than 92%, which is lower than the overall yield in Example 1. In the product stream, the amount of $C_8$ oligomers dropped slightly while the amount of $C_{12}$ oligomers increased slightly. This example demonstrates the process stability of a recycle feed including oxygenates.

TABLE 2 reaction oligomer product distribution:

Recycle feed (see below):

| % C4 | % C5-C7 | % C8 | % C9-C11 | % C12 | % C13-C15 | % C16 | % C20 | % C24 |
|---|---|---|---|---|---|---|---|---|
| 7.00 | 0.54 | 37.40 | 0.91 | 47.47 | 0.30 | 5.96 | 0.40 | 0.02 |

Reaction oligomer product distribution:

| % C4 | % C5-C7 | % C8 | % C9-C11 | % C12 | % C13-C15 | % C16 | % C20 | % C24 |
|---|---|---|---|---|---|---|---|---|
| 7.67 | 0.45 | 36.55 | 0.94 | 48.00 | 0.28 | 5.68 | 0.41 | 0.02 |

Example 3: Extended Time on Stream (TOS) with Oxygenates and Multiple Catalyst Regenerations Catalyst Clariant TiAPSO-34, Total WHSV=2.6, Mass ratio recycle: fresh feed 2:1; Reactor Top 180-185° C., P (psig)=250; 2.9 g Clariant TiAPSO-34 (granular pellets)+glass beads; Typical mass accountability=97.0%; Total Oxygenates in feed: 100 ppm water, 1800 ppm (isobutanol and tert-butyl alcohol at 85/15 mass ratio).

FIG. 1 demonstrates that when a feed stream comprising 33% of recycled feed with oxygenates having an extended time on stream, the percentage of $C_8$ and $C_{12+}$ oligomers is within the range of 30 to 45% and 50% to 65% respectively. Surprisingly, the catalyst can be used for at least 10 days without the need for regeneration and still produce acceptable yields of $C_8$ and $C_{12}$ oligomers. The catalyst is also surprisingly renewable in air and can be used for extended periods without needed to be regenerated. The selective and high yields of $C_8+$ oligomers, length of catalyst use without needing to be replaced, and longer times between catalyst regeneration the allows for a more affordable, stable, and effective process of using a doped Chabazite zeolite catalyst to produce $C_8$-$C_{24}$ oligomers, which can be used in production of renewable jet fuel and renewable diesel fuel.

Example 4: Prophetic Example: Catalyst Regenerated Every 15 Days

Catalyst Clariant TiAPSO-34 regenerated every 15 days at a temperature of 500° C. for about 1.5 hours, Total WHSV=3, Mass ratio recycle: fresh feed 2:1; Reactor Top 200° C., P (psig)=250; 2.9 g Clariant TiAPSO-34 (granular pellets)+glass beads; Typical mass accountability=97.0%; Total Oxygenates in feed: 100 ppm water, 1800 ppm (isobutanol and tert-butyl alcohol at 85/15 mass ratio). Yield of ≥35% of $C_8$ oligomers, ≥50% of $C_{12}$ oligomers, and ≥5% of $C_{16}$ oligomers.

Example 5: Prophetic Example: Higher Oxygenate Concentration

Catalyst Clariant TiAPSO-34, Total WHSV=3.5, Mass ratio recycle: fresh feed 1:1; Reactor Top 185° C., P (psig)=250; 2.9 g Clariant TiAPSO-34 (granular pellets)+glass beads; Typical mass accountability=97.0%; Total Oxygenates in feed: 300 ppm water, 8000 ppm (isobutanol and tert-butyl alcohol at 85/15 mass ratio). Yield of ≥35% of $C_8$ oligomers, ≥50% of $C_{12}$ oligomers, and ≥5% $C_{16}$ oligomers.

Example 6: Prophetic Example: Lower Temperature

Catalyst Clariant TiAPSO-34, Total WHSV=3.5, Mass ratio recycle: fresh feed 3:1; Reactor Top 150° C., P (psig)=250; 2.9 g Clariant TiAPSO-34 (granular pellets)+glass beads; Typical mass accountability=97.0%; Total Oxygenates in feed: 200 ppm water, 6000 ppm (isobutanol and tert-butyl alcohol at 85/15 mass ratio). Yield of ≥35% of $C_8$ oligomers, ≥50% of $C_{12}$ oligomers, and ≥5% $C_{16}$ oligomers.

Example 7: Prophetic Example: Higher Pressure

Catalyst Clariant TiAPSO-34, Total WHSV=3.5, Mass ratio recycle: fresh feed 3:1; Reactor Top 200° C., P (psig)=350; 2.9 g Clariant TiAPSO-34 (granular pellets)+glass beads; Typical mass accountability=97.0%; Total Oxygenates in feed: 200 ppm water, 6000 ppm (isobutanol and tert-butyl alcohol at 85/15 mass ratio). Yield of ≥35% of $C_8$ oligomers, ≥50% of $C_{12}$ oligomers, and ≥5% $C_{16}$ oligomers.

Example 8: Prophetic Example: Higher Pressure and Lower Temperature

Catalyst Clariant TiAPSO-34, Total WHSV=2.5, Mass ratio recycle: fresh feed 3:1; Reactor Top 100° C., P (psig)= 450; 2.9 g Clariant TiAPSO-34 (granular pellets)+glass beads; Typical mass accountability=97.0%; Total Oxygenates in feed: 200 ppm water, 7000 ppm (isobutanol and tert-butyl alcohol at 85/15 mass ratio). Yield of ≥35% of $C_8$ oligomers, ≥50% of $C_{12}$ oligomers, and ≥5% $C_{16}$ oligomers.

The following specific examples are intended to be illustrative and should not be construed as limiting the scope of the invention as defined by appended claims.

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed is:

1. A process for converting one or more $C_2$-$C_8$ linear or branched olefins derived from one or more C2-C5 alcohols to one or more $C_8$-$C_{24}$ hydrocarbons, the process comprising:
   contacting a feed stream comprising the one or more $C_2$-$C_8$ linear or branched olefins and at least 1000 ppm of an oxygenate, with a Chabazite zeolite catalyst at a temperature of 150 to 200° C., a pressure of 200 to 300 psig and a WHSV of between 2 and 3.2; and
   forming the one or more $C_8$-$C_{24}$ hydrocarbons, wherein a yield of the one or more $C_8$-$C_{24}$ hydrocarbons is at least 90% and a selectivity of $C_8$ to $C_{12}$ and larger oligomers is at least 0.35:1, wherein the oxygenate comprises water and at least one alcohol and the Chabazite zeolite catalyst comprises TiAPSO-34.

2. The process of claim 1, further comprising:
   separating and/or blending the one or more $C_8$-$C_{24}$ hydrocarbons to produce a renewable jet fuel or a renewable diesel fuel.

3. The process of claim 1, wherein the one or more C2-C5 alcohols are bio-based and produced by fermentative processes.

4. The process of claim 1, wherein the feed stream further consists of a non-fossil fuel and non-petroleum derived fuel, or a combination thereof.

5. The process of claim 1, wherein the feed stream further comprises:
   a recycled feed stream containing a portion of the one or more $C_8$-$C_{24}$ hydrocarbons.

6. The process of claim 1, wherein the feed stream comprises at least 100 ppm of water.

7. The process of claim 1, wherein the feed stream comprises at least 1000 ppm of the one or more $C_2$-$C_5$ alcohols.

8. The process of claim 7, wherein the one or more $C_2$-$C_5$ alcohols are $C_4$ alcohols.

9. The process of claim 1, wherein the yield of the one or more $C_8$-$C_{24}$ hydrocarbons are at least about 95%.

10. The process of claim 1, wherein the Chabazite zeolite catalyst is regenerated in air every 5 to 20 days.

11. The process of claim 10, wherein the Chabazite zeolite catalyst is regenerated at a temperature of 400 to 600° C.

* * * * *